United States Patent [19]
Arahira et al.

[11] Patent Number: 6,107,471
[45] Date of Patent: Aug. 22, 2000

[54] PLANT-DERIVED, ASPARAGINE RESIDUE-SPECIFIC ENDOPROTEASE CDNA AND A GENE

[75] Inventors: Masaomi Arahira; Chikafusa Fukazawa, both of Tsukuba, Japan

[73] Assignee: Director of National Food Research Institute, Ministry of Agriculture, Forestry and Fisheries, Tsukuba, Japan

[21] Appl. No.: 09/410,028

[22] Filed: Oct. 1, 1999

[30] Foreign Application Priority Data

Nov. 4, 1998 [JP] Japan .................................. 10-327537

[51] Int. Cl.[7] .................................................... C12N 15/29
[52] U.S. Cl. ...................... 536/23.2; 536/23.1; 536/23.6; 435/183; 435/219
[58] Field of Search ..................................... 435/219, 183; 536/23.1, 23.2, 23.6

*Primary Examiner*—Rebecca E. Prouty
*Assistant Examiner*—Richard Hutson
*Attorney, Agent, or Firm*—Oblon, Spivak, McClelland, Maier & Neustadt, P.C.

[57] ABSTRACT

Disclosed are a cDNA encoding a plant-derived, asparagine residue-specific endoprotease having an amino sequence described in SEQ ID NO: 1 in the sequence list and a gene encoding a plant-derived, asparagine residue-specific endoprotease having an amino sequence described in SEQ ID NO: 2 in the sequence listing. The enzymes enable production of asparagine residue-specific endoprotease in large amounts.

3 Claims, No Drawings

6,107,471

PLANT-DERIVED, ASPARAGINE RESIDUE-SPECIFIC ENDOPROTEASE CDNA AND A GENE

FIELD OF THE INVENTION

The present invention relates to a plant-derived, asparagine residue-specific endoprotease cDNA and a gene.

BACKGROUND OF THE INVENTION

Asparagine residue-specific endoproteases refer to enzymes that split peptide etc. in an amino acid sequence of peptide or protein at the C-terminal side of asparagine residue. Among them, the asparagine residue-specific endoprotease derived from plants is called legumaturain.

Although its enzymatic activity was confirmed in various higher plants, legumaturain was highly purified by no other person than the present inventors since it is very unstable.

Storage proteins of plants are synthesized initially as a prepro-protein, which will not be converted into the form of a mature protein until it is under the action of legumaturain. The storage proteins of plants have no problem on safety and are an excellent source of protein so that there is an earnest demand in food industries to produce it on a large scale.

Accordingly, it is also earnestly demanded to produce on a large scale a highly pure legumaturain that is necessary for the synthesis of the storage proteins.

However, from the reason as described above, it has been very difficult to purif y legumaturain and the demand has never been satisfied yet.

SUMMARY OF THE INVENTION

Obtainment and utilization of cDNA and gene of legumaturain ha ve a possibility t o open the way to large-scale production of the targeted enzyme. Also, legumaturain can be utilized in increasing the stability of the targeted enzyme or improvement in enzymatic activity of the targeted enzyme by use of a site-specific mutation method.

Therefore, an object of the present invention is to obtain genetic information of legumaturain and make it possible to produce the targeted enzyme on a large scale.

The present inventors have highly purified legumaturain and tried to clone cDNA and gene of legumaturain based on its amino acid sequence. As a result, they have been successful in elucidating the entire structure of cDNA and gene of legumaturain and thus completed the present invention.

That is, based on the analyses of the amin o acid sequence of highly purified legumaturain, a synthetic oligonucleotide having degeneration was synthesized. Then, mRNA was extracted from an early ripening stage soybean seed and cDNA complementary to the extracted mRNA was prepared. The prepared synthetic oligonucleotide and cDNA were subjected to polymerase chain reaction (PCR) to clone a partial cDNA of legumaturain.

On the other hand, the same mRNA of early ripening stage soybean seed described above was used to synthesize double strand cDNA, which was incorporated into a phage vector by means of an adapter to construct cDNA library.

The partial legumaturain cDNA obtained by the PCr method was labeled before it was used as a probe in screening from the cDNA library to clone a full-length legumaturain cDNA. Analyses of the primary structure of cDNA resulted in the determination of the entire amino acid sequence of legumaturain including a signal peptide sequence.

An oligonucleotide primer based on the cDNA sequence was synthesized and on the other hand each DNA was extracted from germinated soybean and then purified. This was used as a template in a subsequent PCR method to clone a legumaturain gene.

Therefore, according to a first aspect of the present invention, there is provided a cDNA encoding a plant-derived, asparagine residue-specific endoprotease having an amino sequence described in SEQ ID NO: 1 in the sequence listing.

Further, according to a second a spect of the present invention, there is provided a gene encoding a plant-derived, asparagine residue-specific endoprotease having an amino sequence described in SEQ ID NO: 2 in the sequence listing.

Utilization of cDNA and gene according to the present invention enables efficient and large-scale production of an asparagine residue-specific endoprotease (legumaturain), which has been considered difficult to be purified because of its instability.

Furthermore, the present invention can contribute to an increase in the stability of legumaturain, improvement in its enzymatic activity and the like by utilizing a site-specific mutation method.

DETAILED DESCRIPTION OF THE INVENTION

Hereafter, the present invention will be described in detail.

In a first embodiment, the present invention relates to a cDNA that encodes a plant-derived, asparagine residue-specific endoprotease having an amino sequence described in SEQ ID NO: 1 and SEQ ID NO. 2 in the sequence listing.

In the present invention, the plant-derived, asparagine residue-specific endoprotease, i.e., legumaturain, is an enzyme that has an activity of splitting peptide etc. in the amino acid sequence of peptide or protein at the C-terminal side of asparagine residue.

The present inventors were successful in obtaining the above-described cDNA of the present invention as follows.

(1) First, legumaturain contained in plant was extracted and purified.

Legumaturain is contained in storage proteins in various plans, particularly seeds thereof. For example, when legumaturain is to be extracted from soybean seeds, it is preferred to use the seeds between early growing stage and ripe stage, particularly thes e in early growing stage to later growing stage.

Here, to obtain only legumaturain, it is necessary to highly purify a plant as a raw material. For example, plant seeds between early growing stage and ripe stage are pulverized and extracted with a suitable buffer solution and soluble fractions were collected, dialyzed and then subjected to solid-liquid separation. The resultant crude enzyme solution is subjected to hydrophobic chromatography, gel filtration, etc. As a result, substantially pure legumaturain can be obtained by this purification procedure.

(2) Of the amino acid sequence of the resultant purified legumaturain, N-terminal side amino acid sequence was determined. The determination of the amino acid sequence can be carried out by Edman degradation method (PTC method). This can be performed in a simple and easy manner by use of an automatic amino acid sequence analyzer.

(3) On the other hand, besides (2) above, a partial amino acid sequence of purified legumaturain was obtained. First, legumaturain was enzymatically digested to short peptides. Each peptide sample was fractionated with high performance liquid chromatography, etc. and amino acid sequence of each sample, i.e., amino acid sequence of inner portion of legumaturain, was determined.

The determination of amino acid sequence can be carried out in the same manner as described in (2) above.

Among the amino acid sequences thus determined, there were selected two oligonucleotides that have degeneration and these were used as a primer in the PCR reaction described later on (cf. SEQ ID NOS: 3 and 4 in the sequence listing).

(4) Next, RNA was extracted from the plant seeds and cDNA complementary thereto was synthesized. RNA extraction from the plant can be carried out by using the SDS-phenol method according to Fukazawa C. et al., Journal of Biological Chemistry, 200, 6234–6239 (1985).

From the whole extracted RNA was prepared Poly (A)+ RNA, which was subjected to a reverse transcription reaction using a reverse transcriptase using oligo (dT) as a primer to obtain a single strand cDNA.

(5) The single strand cDNA was used as a template and PCR was carried out with the previously prepared synthetic oligonucleotide (SEQ ID NOS: 3 and 4) tocloneapartial cDNA (400 bp) of legumaturain.

The obtained band was subcloned into a vector, which then was analyzed to see if it contained rhe previously analyzed inner amino acid sequence of legumaturain. As a result, said band was confirmed to be a partial cDNA of legumaturain.

(6) Then, a double-stranded cDNA was synthesized using mRNA of the same plant seed and incorporated into a phage vector through an adapter to construct cDNA library.

To make cDNA library, the Okayama-Berg method and the Gubler-Hoffman method can be used. Due to simplicity, the latter method is preferred. Hereafter, description will be made on the case in which the Gubler-Hoffman method was adopted.

First, a double-stranded cDNA is synthesized from the above-mentioned poly(A)+RNA. To the obtained cDNA is ligated an adapter containing restriction enzyme sites such as EcoRI, NotI, BamHI, et. and cDNA is split with restrictio n enzymes. By polyacrylamide gel electrophoresis, cDNA having 500 bp or more were cut and collected from the gel and then adapter was removed therefrom.

Thereafter, a phosphate group was iintroduced to the 5'-position of the resultant nucleotide, which then was split with a restriction enzyme and ligated to λ gt10 phage vector arm (manufactured by Takara Shuzo) which had been previously dephosphorylated. This was packaged in λ phage. In this manner, cDNA library was prepared.

(7) The partial legumaturain cDNA obtained by the PCR method described in (5) above was labeled and used as a probe in screening from the cDNA library described in (6) above. Then, a full-length legumaturain cDNA was cloned.

The screening can be performed by using the previously obtained legumaturain partial cDNA after label ing with a radioisotope, etc. as a probe and conducting plaque hybridization to the cDNA library having about 100,000 plaques.

As a result, of the about 100,000 plaques, several plaques that were found to be positive were separated.

The separated positive plaques after purification were infected to *Escherichia coli* cells and amplified phages, followed by purification of phage particles. The purification of phage DNA can be performed, for example, by ultracentrifugation using CsCl stepwise density gradient.

From the purified phage DNA was split an insert with a restriction enzyme and purified by agarose gel electrophoresis, for example. The product was subcloned in a plasmid vector and then DNA sequencing therefor was performed.

As a result, there was obtained a cDNA having the amino acid sequence described in SEQ ID NO: 1 and SEQ ID NO. 2 of the sequence listing. The cDNA is the cDNA of the present invention according to the first aspect.

Said sequence contains full-length legumaturain. Comparing the database of EMBL, GenBank, etc., revealed that the sequence determined is quite a novel sequence.

The cDNA of the present invention according to the first aspect consists of 1055 bp in full length, of which 14 bp is occupied by polyA. Thenumber of amino acids is in total 241 residues counted from the starting methionine and the number of signal peptides was 21 residues. And there was 220 residues portion from N-terminal sequence of a mature-type protein to C-terminal of an amino acid presumed from the cDNA cloned.

The results of C-terminal analyses and the results of molecular weight measurement by ion spray mass spectrometry indicated that legumaturain is a protein of preprotein-type which receives process on the C-terminal side.

In the sequence, the bonding site of a sugar chain that is involved in the legumaturain activity is the 71st to 78th amino acids portion of the amino acid sequence in the SEQ ID NO: 2 in the sequence listing. The arrangement of this portion is a basic amino acid—hydrophobic amino acid—asparagine (sugar chain)—hydrophobic amino acid—threonine/serine-hydrophobic amino acid—acidic amino acid—cystein from the N-terminal side.

The sugar chain bonding site is considered to participate in the stabilization of legumaturain, which has an ability of specifically splitting an amino acid sequence on the C-terminal side of asparagine residue. Deletion of the sugar chain results in an abrupt decrease in enzymatic activity.

Next, a second embodiment of the present invention will be described.

In a second embodiment, the present invention relates to a full-length gene of legumaturain obtained by primary structure a nalyses of cDNA according to the first aspect of the present invention.

First, two oligonucleotide primers (cf. SEQ ID NOS: 5 and 6 in the listing), i.e., 25 mer and 26 mer, were synthesized based on the base sequence of cDNA in the SEQ ID NO: 1 in the sequence listing.

On the other hand, DNA was prepared from soybean seedlings. The preparation can be performed, for example, by the CTAB method (Fukazawa C. et al., Journal of Biological Chemistry, 200, 6234—6239

With the obtain ed DNA as a template, a PCR method was practiced by using the primers described in SEQ ID NOS: 11 and 12.

As a result, an about 3.1 bp single band was obtained. After subcloning the band in a TA vetor (pCR2.1, manuf actured by invitrogen), DNA sequencing was carried out by the method described above. As a result, the base sequence described in SEQ ID NO: 3 in the sequence listing was obtaineed.

The full-length (cf. SEQ ID NO: 3 of the sequence listing) of the gene of the present invention according to the second aspect is 3077 bp, which is interrupted by four introns to be divided into 5 exons.

The base numbers in respective introns were 67, 705, 1113, and 200 bp, respectively, from the first intron. On the other hand, the base numbers in respective exons were 321, 66, 141, 93, and 420 bp, respectively, from the first exon (cf. SEQ ID NO: 3 in the sequence listing).

The sugar chain bonding site participating in exhibiting activity which was present in the above-mentioned cDNA existed on the first exon (cf. 71st to 78th amino acids in the amino acid sequence described in SEQ ID NO: 3 and SEQ ID NO: 4 in the listing).

The gene encoding the plant-derived, asparagine residue specific endoprotease having the amino acid sequence described in SEQ ID NO: 3 and SEQ ID NO: 4–8 in the sequence listing is the asparagine residue-specific endoprotease gene according to the second aspect of the present invention.

Utilization of the cDNA and gene of the present invention as described above enables large scale and yet efficient production of asparagine residue-specific endoprotease (legumaturain).

Those having amino acid sequences obtainable by deletion, substitution or addition of one or more of amino acid residues in the amino acid sequence described in SEQ ID NO: 1 and 2 in the sequence listing but exhibiting similar effects are encompassed by the present invention. Similarly, those having amino acid sequences obtainable by deletion, substitution or addition of one or more of amino acid residues in the amino acid sequence described in SEQ ID NO: 3 and SEQ ID NO: 4–8 in the sequence listing but exhibiting similar effects are also embraced by the present invention.

EXAMPLES

Hereafter, the present invention will be described in detail by examples. However, the present invention should not be construed as being limited thereto.

Example 1

Determination of Amino Acid Sequence of Legumaturain and Cloning of Partial cDNA by a PCR Methode (1) Preparation of a Template From soybean seeds after 13 days from the flowering were extracted whole RNA by use of the SDS-phenol method as described in Fukazawa C. e t al., Journal of Biological Chemistry, 200, 6234–6239 (1985). Then, Poly (A)+rNA was prepared from the extracted whole RNA using Poly A Tract kit (manufactured by Promega).

Using 1 $\mu$g of the prepared Poly(A)+RNA reverse transcription reaction was performed using oligo(dT) as a primer with 100 U of a reverse transcriptase (RAV-2, manufacture d by Takara Shuzo) at 42° C. for 60 minutes to obtain a single strand cDNA. To decompose the remaining RNA in the reaction mixture, the obtained cDNA was subjected to digestion with alkali (NaOH) overnight at 25° C. in a final concentration of 0.5 N—NaOH. After the decomposition with alkali, the reaction mixture was neutralized with 0.5 M (final concentration) of HEPES buffer solution at pH 7.2 and passed through a gel filtration column ($\phi$0.8 cm×27 cm) packed with Sephadex G-50 (manufactured by Amersham Pharmacia) to remove the decomposed RNA. The thus-obtained single strand cDNA was used in the following PCR method.

(2) Preparation of Primers

The N-terminal amino acid sequence of highly purified legumaturain was determined using gas phase amino acid sequencer (Type 477A, manufactured by Perkin Elmer).

On the other hand, legumaturain was decomposed by the method described by Arahira M. and Fukazawa C., Plant Molecular Biology, 25, 597–6o5 (1994) using V8 protease (manufactured by Takara Shuzo) and lysyl endopeptidase (manufactured by Wako Pure Chemical Industry).

After the decomposition, each sample was fractionated by high performance liquid chromatography column (LC-6AD, manufactured by Shimadzu) connected to a reverse phase column (Silica ODS 120T $\phi$4.6 mm×150 mm, manufactured by Tosoh) in a solvent system with a liner concentration gradient of 0.1% TFA—0.1% TFA/60% acetonitrile.

The obtained peptide was determined for its N-terminal amino acid sequence using a gas phase amino acid sequencer (Type 477A, manufactured by Perkin Elmer) similarly to the determination of N-terminal amino acid sequence and the obtained sequence was defined as an inner amino acid sequence.

Of the amino acid sequences, those sequences that are suitable as a primer for PCR were examined and two primers having degeneracy, 20 mer and 32 mer, were synthesized (cf. SEQ ID NOS: 9 and 10 in the sequence listing).

(3) Legumaturain Partial cDNA Cloning by PCR

Using the oligonucleotide primer synthesized in (2) above, PCR reaction was carried out with the single strand cDNa synthesized in (1) above as a template.

As the conditions for PCR, TaKaRa ExTaq (manufactured by Takara Shuzo) was used in 2.5 U per reaction as a Taq polymerase. The primer was used in a final concentration of 0.4 $\mu$M and dNTP mix was used in a final concentration of 0.2 mM. The single strand cDNA as a template was used in an amount of 10 ng.

The gene amplifying apparatus used is TaKaRa PCR Thermal Cycler 480 (manufactured by Takara Shuzo), which was operated at a denaturation temperature of 95° C. for 30 seconds and at an annealing temperature of 56° C. for 30 seconds, an elongation reaction temperature of 72° C. for 1 minute and 30 seconds at 35 cycles.

As a result, an about 400 bp single band was obtained, and then subcloned in a TA vector ([pCR2.1] (manufactured by Invitrogen) From the cloned *Escherichia coli* cells were prepared plasmid DNA according to the conventional method (Maniatis T. et al., "Molecular Cloning" C.old Spring Har bor Labo. (1982).

The prepared plasmid was subjected to fluorescence autoseqencing using a DNA sequencer DSQ1000 manufactured by Shimadzu. As a result, it revealed that the subcloned band contained the inner amino acid sequence of legumaturain that were determined in (2) above.

This confirmed that the cloned band was a partial cDNA of legumaturain.

Example 2

Preparation of cDNA Library of Soybean in Early Growing Stage

From 2.5 $\mu$g of the poly(A)+RNA obtained in Example 1 (1) was synthesized double-stranded DNA using a cDNA synthesis kit (manufactured by Amersham Pharmacia) which was based on the principle of Gubler-Hoffman method while monitoring the progress of synthesis with addition of [$^{32}$P]-dCTP.

One (1) nmol of EcoRI-NotI-BamHI adapter (manufactured by Takara Shuzo) was ligated to the double-stranded cDNA using a ligation pack manufactured by Nippon Gene. The cDNA was subjected to polyacrylamide gel electrophoresis according to the method described by Fukazawa C. et al., Journal of Biological Chemistry, 200, 6234–6239 (1985) to obtain cDNA having 500 bp length or more by cutting gel, and the adapter was removed.

Since the adapter contains no phosphate at the 5'-position, a phosphate group was introduced by use of T4 polynucleotide kinase (manufactured by Nippon Gene).

Thereafter, the cDNA was split with EcoRI and the resulting fragments were ligated to λgt10 phage vector arm (Takara Shuzo) previously dephosphorylated in the same manner as described above with the ligation pack manufactured by Nippon Gene and then packaged in λphage using an in vitro packaging kit (Amersham Pharmacia).

Thus, soybean grown seed (13 days after the flowering) cDNA library was prepared.

Example 3

Cloning of Full-length Legumaturain cDNA

Legumaturain partial cDNA obtained in Example 1 was labeled by a PCR method with [$^{32}$P]-dCTP according to the method of Arahira M. and Fukazawa C., Plant Molecular Biology, 25, 597–605 (1994)

This was used as a probe and plaque hybridization was practiced from the library of soybean grown seed (13 days after the flowering) prepared in Example 2 according to the method described by Arahira M. and Fukazawa C., Plant Molecular Biology, 25, 597–605 (1994). As a result, several positive plaques were separated from about 100,000 plaques of cDNA.

The positive plaques were purified and infected to *Escherichia coli* cells to amplify the phage and the phage particles were purified by ultracentrifugation using CsCl stepwise density gradient to obtain purified phage DNA.

The purified phage DNA was split with BamHI to obtain an insert, which was purified from agarose gel and then subcloned in pUC19 plasmid vector. Thereafter, DNA s equencing was practiced in the same manner as in Example 1.

Results of analyses revealed that the resultant cDNA contained full-length legumaturain sequence and contained the base sequence and amino acid sequence described in SEQ ID NO: 1 in the sequence listing. Comparison with the databases of EmBL, GenBanke etc. indicated that the cDNA is of quite a novel sequence.

The total length of the cDNA is 1055 bp, of which 14 bp is occupied by poly A. The number of amino acids is in total 241 residues co unted from the starting methionine. The number of amino acids of s ignal peptide is 21 residues.

There was 220 residues portion from N-terminal sequence of a ma ture-type protein to C-terminal of an amino acid presumed from the cDNA cloned. Th e results of C-terminal analyses and the results of molecular weight measurement by ion spray mass spectrometry indicated that legumaturain is a protein of preprotein-type which receives process on the C-terminal side.

In the sequence, the bonding site of a sugar chain that is involved in the legumaturain activity was only one (the 71st to 78th amino acids portion of the amino acid sequence in the SEQ ID NO: 1 and SEQ ID NO: 2 in the sequence listing). The arrangement of this bonding site was found to be a basic amino acid (arginine)—hydrophobic amino acid (alanine)—asparagine (sugar chain)—hydrophobic amino acid (alanine)—threonine/serine—hydrophobic amino acid (phenylalanine)—acidic amino acid (aspartic acid)—cystein.

Example 4

Legumaturain Gene Cloning

Based on the base sequence of the cDNA obtained in Example 3, two types of 25 mer and 26 mer oligonucleotide primers were synthesized (cf. SEQ ID NOS: 11 and 12 in the sequence listing).

Nuclear DNA was prepared from soybean seedlings by the CTAB method (Fukazawa C. et al., Nucleic Acid Research, 8117 (1987)). Using 10 ng of the DNA as a template, PCR method was practiced under the same conditions as in Example 1.

As a result, an about 3.1 kbp sin gle band was obtained. This was subcloned in a TA vector [pCR 2.1] (manufactured by Invitrogen) and then DNA sequencing thereof was carried out by th e method described in Example 3. Results of analyses indicated that the cloned gene had the same base sequence as described in SEQ ID NO: 3 in the sequence listing.

The full-length of the gene was found to be 3077 bp, which was interrupted by four introns to be divided into 5 exons. The base numbers in respective introns were 67, 705, 1113, and 200 bp, respectively, from the first intron. On the other hand, the base numbers in respective exons were 321, 66, 141, 93, and 420 bp, respectively, from the first exon (cf. SEQ ID NO: 3 in the sequence listing)—Note that the sugar chain bonding site participating in exhibiting activity existed on the first exon.

What is claimed is:

1. A isolated and purified polynucleotide encoding a plant-derived, asparagine residue-specific endoprotease having an amino acid sequence described in SEQ ID NO: 2.

2. An isolated and purified polynucleotide of claim 1, wherein said polynucleotide is the cDNA described in SEQ ID NO: 1.

3. An isolated and purified polynucleotide of claim 1, wherein said polynucleotide is a genomic DNA described in SEQ ID NO: 3.

* * * * *

SEQUENCE LISTING

```
<160> NUMBER OF SEQ ID NOS: 12

<210> SEQ ID NO 1
<211> LENGTH: 1055
<212> TYPE: DNA
<213> ORGANISM: Glycine max
<220> FEATURE:
<221> NAME/KEY: CDS
<222> LOCATION: (85)..(810)

<400> SEQUENCE: 1
ttggtggtag ctgttacgag tcagcaagag agaaatatct tgttgagttg atttctgatc      60
```

-continued

```
ccaaattgag tttgagtttc agcc atg gta tct gtt tct ctg ctc tta ttc       111
                          Met Val Ser Val Ser Leu Leu Leu Phe
                           1               5 cta tct ttc ttt gcc ttc ttt gca ccc tct gaa tct cac gac aaa gtc       159
Leu Ser Phe Phe Ala Phe Phe Ala Pro Ser Glu Ser His Asp Lys Val
 10              15                  20                  25 tcg ttg gaa ttg tac tac gaa agc tta tgc ccc tac agc gcc aac ttc       207
Ser Leu Glu Leu Tyr Tyr Glu Ser Leu Cys Pro Tyr Ser Ala Asn Phe
                 30                  35                  40 atc gtg aat cac ctc cca aaa atc ttc acc cca gat ctt gcc cca atc       255
Ile Val Asn His Leu Pro Lys Ile Phe Thr Pro Asp Leu Ala Pro Ile
             45                  50                  55 gtt cac ctc aaa ctc gtt cct tgg ggc aat gcc aaa ctc cgt gcc aac       303
Val His Leu Lys Leu Val Pro Trp Gly Asn Ala Lys Leu Arg Ala Asn
         60                  65                  70 gcc acc ttt gac tgc cag cat ggg cca tat gag tgc ttg ctg aac aca       351
Ala Thr Phe Asp Cys Gln His Gly Pro Tyr Glu Cys Leu Leu Asn Thr
     75                  80                  85 gtt gaa gcc tgt gca att cac atc tgg cct caa ctc agc aaa cat ttt       399
Val Glu Ala Cys Ala Ile His Ile Trp Pro Gln Leu Ser Lys His Phe
 90                  95                 100                 105 cct ttc atc tac tgt gtt gag gat ctg gtg ttt cag agt aag cgt gag       447
Pro Phe Ile Tyr Cys Val Glu Asp Leu Val Phe Gln Ser Lys Arg Glu
                110                 115                 120 gaa tgg gaa tct tgt ttt gag aaa ctg gat ctt gat tcg gaa cct att       495
Glu Trp Glu Ser Cys Phe Glu Lys Leu Asp Leu Asp Ser Glu Pro Ile
            125                 130                 135 aat cag tgt tat aat agt gaa cat gga aaa cag ttg gag cta caa tat       543
Asn Gln Cys Tyr Asn Ser Glu His Gly Lys Gln Leu Glu Leu Gln Tyr
        140                 145                 150 gca gct gaa aca agt gct ctg gag cct cct cac aag tat gtt cct tgg       591
Ala Ala Glu Thr Ser Ala Leu Glu Pro Pro His Lys Tyr Val Pro Trp
    155                 160                 165 gta gtt gtg gat gga gaa cca ctc tat gag gat tat gag aac ttc tta       639
Val Val Val Asp Gly Glu Pro Leu Tyr Glu Asp Tyr Glu Asn Phe Leu
170                 175                 180                 185 agc tat ctt tgt aag gct tat aaa ggc act gtt aca ccc caa agt tgc       687
Ser Tyr Leu Cys Lys Ala Tyr Lys Gly Thr Val Thr Pro Gln Ser Cys
                190                 195                 200 acc caa gca tca tac cta aga gaa gtg aat gca aag cct aag cat tcg       735
Thr Gln Ala Ser Tyr Leu Arg Glu Val Asn Ala Lys Pro Lys His Ser
            205                 210                 215 gtt tgc tac aag gac agt ggg att atg cta aca tgg gaa aaa gtg agg       783
Val Cys Tyr Lys Asp Ser Gly Ile Met Leu Thr Trp Glu Lys Val Arg
        220                 225                 230 tca acc att gca tca tgg atg cac tag atgaatcttg gcagtgcatt            830
Ser Thr Ile Ala Ser Trp Met His
    235                 240 ttagatgtgc aatgctgca tttagtagca gtttgttcgt gttatcttgt gtgtagttgt      890
gttgatccct ccaaaagtgc aaatagaact tgtgatgcac ataaaaccat atcgtactct     950
cataaaaaaa ataaaaccat gatgtgtatg tgtatgaggt acttaagtac aatatatata    1010
gagagagaaa aaaaaaagta agtgcaattc taaaaaaaaa aaaaa                    1055
```

<210> SEQ ID NO 2
<211> LENGTH: 241
<212> TYPE: PRT
<213> ORGANISM: Glycine max

<400> SEQUENCE: 2

```
Met Val Ser Val Ser Leu Leu Leu Phe Leu Ser Phe Phe Ala Phe Phe
 1               5                  10                  15

Ala Pro Ser Glu Ser His Asp Lys Val Ser Leu Glu Leu Tyr Tyr Glu
            20                  25                  30

Ser Leu Cys Pro Tyr Ser Ala Asn Phe Ile Val Asn His Leu Pro Lys
        35                  40                  45

Ile Phe Thr Pro Asp Leu Ala Pro Ile Val His Leu Lys Leu Val Pro
    50                  55                  60

Trp Gly Asn Ala Lys Leu Arg Ala Asn Ala Thr Phe Asp Cys Gln His
 65                 70                  75                  80

Gly Pro Tyr Glu Cys Leu Leu Asn Thr Val Glu Ala Cys Ala Ile His
                85                  90                  95

Ile Trp Pro Gln Leu Ser Lys His Phe Pro Phe Ile Tyr Cys Val Glu
            100                 105                 110

Asp Leu Val Phe Gln Ser Lys Arg Glu Glu Trp Glu Ser Cys Phe Glu
        115                 120                 125

Lys Leu Asp Leu Asp Ser Glu Pro Ile Asn Gln Cys Tyr Asn Ser Glu
    130                 135                 140

His Gly Lys Gln Leu Glu Leu Gln Tyr Ala Ala Glu Thr Ser Ala Leu
145                 150                 155                 160

Glu Pro Pro His Lys Tyr Val Pro Trp Val Val Asp Gly Glu Pro
                165                 170                 175

Leu Tyr Glu Asp Tyr Glu Asn Phe Leu Ser Tyr Leu Cys Lys Ala Tyr
            180                 185                 190

Lys Gly Thr Val Thr Pro Gln Ser Cys Thr Gln Ala Ser Tyr Leu Arg
    195                 200                 205

Glu Val Asn Ala Lys Pro Lys His Ser Val Cys Tyr Lys Asp Ser Gly
    210                 215                 220

Ile Met Leu Thr Trp Glu Lys Val Arg Ser Thr Ile Ala Ser Trp Met
225                 230                 235                 240

His
```

```
<210> SEQ ID NO 3
<211> LENGTH: 3077
<212> TYPE: DNA
<213> ORGANISM: Glycine max
<220> FEATURE:
<221> NAME/KEY: CDS
<222> LOCATION: (85)..(321)
<220> FEATURE:
<221> NAME/KEY: CDS
<222> LOCATION: (389)..(454)
<220> FEATURE:
<221> NAME/KEY: CDS
<222> LOCATION: (1160)..(1300)
<220> FEATURE:
<221> NAME/KEY: CDS
<222> LOCATION: (2414)..(2506)
<220> FEATURE:
<221> NAME/KEY: CDS
<222> LOCATION: (2707)..(2895)
```

<400> SEQUENCE: 3

```
ttggtggtag ctgttacgag tcagcaagag agaaatatct tgttgagttg atttctgatc      60
ccaaattgag tttgagtttc agcc atg gta tct gtt tct ctg ctc tta ttc     111
                         Met Val Ser Val Ser Leu Leu Leu Phe
                          1               5
```

-continued

```
cta tct ttc ttt gcc ttc ttt gca ccc tct gaa tct cac gac aaa gtc      159
Leu Ser Phe Phe Ala Phe Phe Ala Pro Ser Glu Ser His Asp Lys Val
 10              15                  20                  25 tcg ttg gaa ttg tac tac gaa agc tta tgc ccc tac agc gcc aac ttc      207
Ser Leu Glu Leu Tyr Tyr Glu Ser Leu Cys Pro Tyr Ser Ala Asn Phe
                 30                  35                  40 atc gtg aat cac ctc cca aaa atc ttc acc cca gat ctt gcc cca atc      255
Ile Val Asn His Leu Pro Lys Ile Phe Thr Pro Asp Leu Ala Pro Ile
             45                  50                  55 gtt cac ctc aaa ctc gtt cct tgg ggc aat gcc aaa ctc cgt gcc aac      303
Val His Leu Lys Leu Val Pro Trp Gly Asn Ala Lys Leu Arg Ala Asn
         60                  65                  70 gcc acc ttt gac tgc cag gtactctctt ctccaatctt atacacactc             351
Ala Thr Phe Asp Cys Gln
     75 ttcacctatt tttatttaat tctgatgaca attgcag cat ggg cca tat gag tgc     406
                                        His Gly Pro Tyr Glu Cys
                                             80              85 ttg ctg aac aca gtt gaa gcc tgt gca att cac atc tgg cct caa ctc      454
Leu Leu Asn Thr Val Glu Ala Cys Ala Ile His Ile Trp Pro Gln Leu
                 90                  95                 100 gtaagtaaca attgctgtgc ctttgcccct ttctttcttt ctttcttttt tcttttttct    514
ttgatttggg atcagaactt aagaatgctt ttttttattat tataatatta tgttattatt   574
acggattatt cagcatcgat ttttttcagat gattaattt tattggattt tgattaggtt    634
attttcttcc aattatttt tttatccaaa aaggagatga agttgttggt gaacttagga    694
gtgcctttat tattattgtt attatgttat tgttaaggag tattcattga tttatagat    754 gattaatttt cattggatca cctttgatta ggttattttcc tttcaattat tttattttt   814 atgaaaaagg agatgaagtc tggtgccacc tggacgaatg agttgttggt gaacttagaa   874
gtactattat aattatgata aattttgaaa ataaaaata aaaaggagt acttttggtc     934 agtgtaacag tgctttagaa agatgctcta gcttgagcac tgtgcttaag ttgctataaa   994
ttcctgttat ccgagtttga ttcctatgga taaagttgtt attataaatt cttggcacct  1054
gagttcgagt tcaatttgta cggataaaaa agtttagcag tgctttgcat gtgtacctcg  1114
gtatctctgt tatgagtgtt ttatgtaaat cacactcttt tgcag agc aaa cat ttt   1171
                                              Ser Lys His Phe
                                                          105 cct ttc atc tac tgt gtt gag gat ctg gtg ttt cag agt aag cgt gag    1219
Pro Phe Ile Tyr Cys Val Glu Asp Leu Val Phe Gln Ser Lys Arg Glu
             110                 115                 120 gaa tgg gaa tct tgt ttt gag aaa ctg gat ctt gat tcg gaa cct att    1267
Glu Trp Glu Ser Cys Phe Glu Lys Leu Asp Leu Asp Ser Glu Pro Ile
         125                 130                 135 aat cag tgt tat aat agt gaa cat gga aaa cag gttggtgttt ttctctgatt  1320
Asn Gln Cys Tyr Asn Ser Glu His Gly Lys Gln
     140                 145 tcgctcttgt ccttgcttga gctaccatgt tgtgattgag atagtattat gtacattagt   1380
ttagttttca tgccctccga gtgtaagtat gacttgtaaa ctagttacta caaagtattc   1440
taagatccta tttggataaa atttgttaca aatacttgca ggtgaagaaa ataagaagat   1500
aaaataaatt gagttttcct tccgtgagtt aaaatcaaat caacttcggc acctcggatt   1560
ttggaagagt taaatgagac tgagaacttt tatggaagtt tagtgttaag ttgattttag   1620
cttgtgagag aagctcaatt tatttttactt tcttattttc tcatcttata agtgcttatg  1680
aaaaagttga tctaaacagg acttaaaatg ttttttaacta accttttctct tctatggttg  1740
```

```
tttttttatga accttaaagt tatactaaca ttgctaaatg atacaagcta gtggaaagtt      1800
gggaattaga aaatttgaac agttatacag ttacagggtt ggtggtgact tctcaattcc      1860
ttatttaaac taatcttaag tgtcatagat aattgaatct tcttcgaggt gagatataat      1920
ccatgtcaac tagccgtaac tgggctctgt tatgtgaaac ttggatggta aggtctggta      1980
tttgttatgt gccggtctac tactttgctt ttattcttca agacaacaaa atgaaatagc      2040
taatgagaag taattttaac ttattccagc aattacttca aaaattggtc atgttcttca      2100
tttttacaaa actctaaagc agtgtaatat gatctacaaa ttaccttatt gtcatacatg      2160
attgctcttt gctacagata ctgccacacg atctaataga actgccaatt tgtagcttct      2220
gaacattcat ctttcttcaa gctaatttct caaaatcctt tttcaatctt gctgaatgtg      2280
aagactatct cttgatgaaa acaaaacat  atgacagatg tgctgaatac atcattgttt      2340
gactggaatt ttgtctcaag tagcatttac tatcttgttt tgatcattag taacatttac      2400
```

```
tatctttatg tag ttg gag cta caa tat gca gct gaa aca agt gct ctg        2449
            Leu Glu Leu Gln Tyr Ala Ala Glu Thr Ser Ala Leu
                150             155             160 gag cct cct cac aag tat gtt cct tgg gta gtt gtg gat gga gaa cca      2497
Glu Pro Pro His Lys Tyr Val Pro Trp Val Val Val Asp Gly Glu Pro
165             170             175 ctc tat gag gtcagttttg caattttata tcggctgaac caagccccat                 2546
Leu Tyr Glu tcccagtgtt tggaatttc  actaaaaaat acttctaatt aacaaataac ttataacact      2606
gaaatttgtg ttttacatat gtaagttgtg ttatattaat gaatcgaatt agaagtgtac      2666
aggaaattca aaaagaactt gcaaatttct tttgctgcag gat tat gag aac ttc      2721
                                                Asp Tyr Glu Asn Phe
                                                             180 tta agc tat ctt tgt aag gct tat aaa ggc act gtt aca ccc caa agt     2769
Leu Ser Tyr Leu Cys Lys Ala Tyr Lys Gly Thr Val Thr Pro Gln Ser
185             190             195             200 tgc acc caa gca tca tac cta aga gaa gtg aat gca aag cct aag cat     2817
Cys Thr Gln Ala Ser Tyr Leu Arg Glu Val Asn Ala Lys Pro Lys His
                205             210             215 tcg gtt tgc tac aag gac agt ggg att atg cta aca tgg gaa aaa gtg     2865
Ser Val Cys Tyr Lys Asp Ser Gly Ile Met Leu Thr Trp Glu Lys Val
            220             225             230 agg tca acc att gca tca tgg atg cac tag atgaatcttg gcagtgcatt         2915
Arg Ser Thr Ile Ala Ser Trp Met His
            235             240
```

```
ttagatgtgc caatgctgca tttagtagca gtttgttcgt gttatcttgt gtgtagttgt      2975
gttgatccct ccaaaagtgc aaatagaact tgtgatgcac ataaaaccat atcgtactct      3035
cataaaaaaa ataaaaccat gatgtgtatg tgtatgaggt ac                        3077
```

<210> SEQ ID NO 4
<211> LENGTH: 79
<212> TYPE: PRT
<213> ORGANISM: Glycine max

<400> SEQUENCE: 4

Met Val Ser Val Ser Leu Leu Leu Phe Leu Ser Phe Phe Ala Phe Phe
 1               5                  10                  15

Ala Pro Ser Glu Ser His Asp Lys Val Ser Leu Glu Leu Tyr Tyr Glu
             20                  25                  30

-continued

Ser Leu Cys Pro Tyr Ser Ala Asn Phe Ile Val Asn His Leu Pro Lys
            35                  40                  45

Ile Phe Thr Pro Asp Leu Ala Pro Ile Val His Leu Lys Leu Val Pro
     50                  55                  60

Trp Gly Asn Ala Lys Leu Arg Ala Asn Ala Thr Phe Asp Cys Gln
 65              70                  75

<210> SEQ ID NO 5
<211> LENGTH: 22
<212> TYPE: PRT
<213> ORGANISM: Glycine max

<400> SEQUENCE: 5

His Gly Pro Tyr Glu Cys Leu Leu Asn Thr Val Glu Ala Cys Ala Ile
 1               5                  10                  15

His Ile Trp Pro Gln Leu
             20

<210> SEQ ID NO 6
<211> LENGTH: 47
<212> TYPE: PRT
<213> ORGANISM: Glycine max

<400> SEQUENCE: 6

Ser Lys His Phe Pro Phe Ile Tyr Cys Val Glu Asp Leu Val Phe Gln
 1               5                  10                  15

Ser Lys Arg Glu Glu Trp Glu Ser Cys Phe Glu Lys Leu Asp Leu Asp
             20                  25                  30

Ser Glu Pro Ile Asn Gln Cys Tyr Asn Ser Glu His Gly Lys Gln
         35                  40                  45

<210> SEQ ID NO 7
<211> LENGTH: 31
<212> TYPE: PRT
<213> ORGANISM: Glycine max

<400> SEQUENCE: 7

Leu Glu Leu Gln Tyr Ala Ala Glu Thr Ser Ala Leu Glu Pro Pro His
 1               5                  10                  15

Lys Tyr Val Pro Trp Val Val Asp Gly Pro Leu Tyr Glu
             20                  25                  30

<210> SEQ ID NO 8
<211> LENGTH: 62
<212> TYPE: PRT
<213> ORGANISM: Glycine max

<400> SEQUENCE: 8

Asp Tyr Glu Asn Phe Leu Ser Tyr Leu Cys Lys Ala Tyr Lys Gly Thr
 1               5                  10                  15

Val Thr Pro Gln Ser Cys Thr Gln Ala Ser Tyr Leu Arg Glu Val Asn
             20                  25                  30

Ala Lys Pro Lys His Ser Val Cys Tyr Lys Asp Ser Gly Ile Met Leu
         35                  40                  45

Thr Trp Glu Lys Val Arg Ser Thr Ile Ala Ser Trp Met His
     50                  55                  60

<210> SEQ ID NO 9
<211> LENGTH: 20
<212> TYPE: DNA
<213> ORGANISM: Artificial Sequence -continued

```
<220> FEATURE:
<223> OTHER INFORMATION: Description of Artificial Sequence:primer

<400> SEQUENCE: 9
gcnaayttya thgtnaayca                                              20

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 10
tcnccrtcna cnacnaccca nggnacrtay tt                                32

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 11
ttggtggtag ctgttacgag tcagc                                        25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 12
gtacctcata cacatacaca                                              20
```